(12) United States Patent
Reinschke

(10) Patent No.: US 9,125,576 B2
(45) Date of Patent: Sep. 8, 2015

(54) SEPARATING ENDOSCOPY CAPSULE FROM SURFACE OF LIQUID

(75) Inventor: Johannes Reinschke, Nürnberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 331 days.

(21) Appl. No.: 13/138,355

(22) PCT Filed: Dec. 9, 2009
(Under 37 CFR 1.47)

(86) PCT No.: PCT/EP2009/066754
§ 371 (c)(1),
(2), (4) Date: Aug. 5, 2011

(87) PCT Pub. No.: WO2010/088991
PCT Pub. Date: Aug. 12, 2010

(65) Prior Publication Data
US 2012/0022328 A1    Jan. 26, 2012

(30) Foreign Application Priority Data

Feb. 5, 2009 (DE) .......................... 10 2009 007 513

(51) Int. Cl.
| | |
|---|---|
| *A61B 1/00* | (2006.01) |
| *A61B 1/04* | (2006.01) |
| *A61B 1/06* | (2006.01) |
| *A61B 5/06* | (2006.01) |
| *A61B 19/00* | (2006.01) |

(52) U.S. Cl.
CPC .............. *A61B 1/041* (2013.01); *A61B 1/00158* (2013.01); *A61B 5/062* (2013.01); *A61B 19/22* (2013.01); *A61B 2019/2253* (2013.01); *A61B 2019/2261* (2013.01)

(58) Field of Classification Search
CPC ............... A61B 1/041; A61B 1/00147; A61B 1/00158; A61B 1/00016; A61B 1/00032

USPC .................. 600/109, 117, 118, 160, 407, 476
See application file for complete search history.

(56) References Cited

U.S. PATENT DOCUMENTS

2007/0221233 A1* 9/2007 Kawano et al. ................ 128/899
2008/0294006 A1* 11/2008 Uchiyama et al. ............ 600/118
(Continued)

FOREIGN PATENT DOCUMENTS

| | | |
|---|---|---|
| CN | 101351148 A | 1/2009 |
| EP | 1 972 255 A1 | 9/2008 |

(Continued)

OTHER PUBLICATIONS

Office Action issued Mar. 26, 2013 in corresponding Chinese Patent Application No. 200980156172.5.
(Continued)

*Primary Examiner* — Anhtuan T Nguyen
*Assistant Examiner* — William Chou
(74) *Attorney, Agent, or Firm* — Staas & Halsey LLP

(57) ABSTRACT

A magnetically guided endoscopy capsule is separated from the surface of water with the aim of immersing the capsule completely in water, using the least possible magnetic force. A brief force curve (F_mag(t)) is thereby automatically generated on the capsule by a solenoid system, by one or more force pulses. Assuming that the capsule floats on the water surface at the start of the force curve, a force curve is applied generating an odd number of force pulses having a step profile. Each odd force pulse brings about at least a partial immersion of the endoscopy capsule in the liquid, and each even force pulse bring about at least a partial emersion of the endoscopy capsule out of the liquid.

16 Claims, 3 Drawing Sheets

(56) References Cited

U.S. PATENT DOCUMENTS

| | | |
|---|---|---|
| 2008/0300453 A1 | 12/2008 | Aoki et al. |
| 2010/0010304 A1* | 1/2010 | Kawano .................. 600/117 |
| 2011/0034795 A9* | 2/2011 | Gilad et al. ............... 600/407 |

FOREIGN PATENT DOCUMENTS

| | | |
|---|---|---|
| EP | 2 143 368 A1 | 1/2010 |
| WO | 2008/062594 A1 | 5/2008 |
| WO | 2009/001666 A1 | 12/2008 |

OTHER PUBLICATIONS

German Office Action for Application No. 10 2009 007 513.5-35 dated Sep. 25, 2009.

International Search Report for PCT/EP2009/066754; mailed Apr. 28, 2010.

* cited by examiner

SEPARATING ENDOSCOPY CAPSULE FROM SURFACE OF LIQUID

CROSS REFERENCE TO RELATED APPLICATIONS

This application is the U.S. national stage of International Application No. PCT/EP2009/066754, filed Dec. 9, 2009 and claims the benefit thereof. The International Application claims the benefits of German Application No. 102009007513.5 filed on Feb. 5, 2009, both applications are incorporated by reference herein in their entirety.

BACKGROUND

Described below is a method and a device for separating a magnetically guided endoscopy capsule from a water surface with the aim of immersing the capsule completely in water and thereby separating the capsule from the water surface, using the least possible magnetic force.

The use of endoscopy capsules is increasingly widely applied in medicine for diagnosing or treating the inside of a patient. An endoscopy capsule may contain, amongst other things, medical instruments, for example for carrying out a biopsy or for introducing medication into the body, and/or imaging systems such as cameras. The endoscopy capsule has a magnetic element which is fixedly connected to the capsule and includes a magnetic dipole moment which may originate, for example, from a permanent magnet fixedly installed in the capsule. Due to the magnetic dipole moment the capsule may be maneuvered and/or navigated in any manner by a maneuvering device, as disclosed, for example, in DE 10 2008 004 871.

DE 10 2008 004 871 discloses a solenoid system consisting of a plurality of individual coils for navigating an endoscopy capsule, a video capsule or any other probe. Hereinafter simply an "endoscopy capsule" is generally referred to, or in brief a "capsule", the endoscopy capsule, the video capsule and the other probes being incorporated within this term. A magnetic element, for example a permanent magnet or ferromagnet, is fixedly installed in the capsule so that it may be maneuvered in any manner by the solenoid system. The solenoid system generates magnetic field components $B_x$, $B_y$, $B_z$ along the x, y, z axes of a Cartesian coordinate system and magnetic gradient fields which permit contactless guidance of the endoscopy capsule.

In this case—in the absence of significant mechanical counter forces—use is made of the fact that the magnetic element, i.e. a body with a magnetic dipole moment $\vec{m}$, is oriented parallel to the direction of the magnetic field $\vec{B}$, formed by the magnetic field components $B_x$, $B_y$, $B_z$ in the direction of the axes of the Cartesian coordinate system. As the magnetic element is fixedly connected to the endoscopy capsule, the orientation of the capsule may be influenced in this manner. Additionally, triggered by the magnetic gradient fields $\partial B_x/\partial x$ etc. a force $\vec{F} = \underline{G} \cdot \vec{m}$ acts on the magnetic dipole moment $\vec{m}$ with a gradient matrix $\underline{G}$ comprising the gradient fields according to $$\vec{F} = \underline{G} \cdot \vec{m} = \begin{pmatrix} \frac{\partial B_x}{\partial x} & \frac{\partial B_x}{\partial y} & \frac{\partial B_x}{\partial z} \\ \frac{\partial B_y}{\partial x} & \frac{\partial B_y}{\partial y} & \frac{\partial B_y}{\partial z} \\ \frac{\partial B_z}{\partial x} & \frac{\partial B_z}{\partial y} & \frac{\partial B_z}{\partial z} \end{pmatrix} \cdot \vec{m}$$

The gradient matrix $\underline{G}$ is symmetrical and trace-free due to the Maxwell equations rot $\vec{B}=0$ and div $\vec{B}=0$, i.e. it contains with $\partial B_x/\partial y$ ($=\partial B_y/\partial x$), $\partial B_x/\partial z$ ($=\partial B_z/\partial x$), $\partial B_y/\partial z$ ($=\partial B_z/\partial y$) and two of the three diagonal elements (for example $\partial B_x/\partial x$ and $\partial B_y/\partial y$) five independent gradient fields.

The magnetic field $\vec{B}$ and one or more of the gradient fields of the matrix $\underline{G}$ may be set in any manner via a targeted activation of the individual coils of the solenoid arrangement. It is, therefore, possible firstly to rotate the magnetic element and/or the capsule and thus to align the magnetic element and/or the capsule in any manner in a work space A within the solenoid system. Secondly, it is possible to exert a force $\vec{F}$ on the magnetic element in order to shift it translationally in addition to the rotation.

For a more detailed explanation of the navigation of the capsule by the various fields generated by the solenoid system, reference is made in particular to DE 10 2008 004 871.

A specific application of magnetic capsule endoscopy is so-called stomach screening which involves an examination of the stomach and is disclosed, for example, in US 2007/0221233 A1. In stomach screening, the stomach is partially filled with water and the capsule and/or a camera integrated into the capsule is intended to take long-distance and close-up images of the stomach lining, the optical axis of the camera generally being oriented in the direction of the longitudinal axis of the capsule and generally being fitted into the capsule at one of the capsule ends. With long-distance images, the capsule generally floats on the water surface, one of the two generally semi-spherical capsule ends partially protruding from the water surface. For close-up images, the capsule is typically completely immersed in water. For the transition from long-distance images to close-up images, the capsule consequently has to be separated from the water surface, for which a magnetic force has to be applied to the capsule in the order of approximately 2 mN due to the surface tension of the water. This separation force is markedly greater than the magnetic force which is required to move the capsule slowly, i.e. in the case of stomach screening at a speed of 0-5 mm/sec, either in two dimensions on the water surface or three-dimensionally, completely immersed in the water. Typically, forces are required here in the order of approximately 0.2 mN to 0.3 mN, this only being applicable with a vertical movement of a capsule completely immersed in water, when the average density of the capsule is approximately the same as the density of water.

The exerted magnetic force is proportional to the coil currents in the individual coils of the solenoid system. In order to generate the magnetic force on the capsule required for complete immersion, accordingly coil currents and/or a number of ampere turns are required in the magnetic coils which markedly exceed the currents and/or number of ampere turns required for normal navigation of the capsule. Accordingly, expensive power amplifiers which can generate the higher currents are required and correspondingly more efficient cooling systems.

One possibility for reducing the influence of the surface tension is to pivot the capsule floating on the water surface such that the end protruding from the water surface is wetted with water. After wetting, the capsule behaves as a completely immersed capsule which floats just below the water surface, i.e. a specific separation force is no longer required for lowering the capsule. When pivoted, however, inevitably the viewing angle of the capsule and/or of the area reproduced by the camera is altered. Accordingly, the target area of the stomach lining which is to be observed more closely and which, for example, has been identified by the long-distance images, generally moves out of the field of view of the camera when pivoted. The target area then has to be found again before it is possible to continue with the more detailed examination which with the relatively low image refresh rate of the capsule camera and under the optical conditions in the stomach may be very time-consuming.

SUMMARY

Therefore, an aspect is to specify a method and a device for the complete immersion of an endoscopy capsule below a surface of a liquid.

In the solution described below, the time characteristic of the force which is generated by the solenoid system on the capsule and/or the magnetic moment thereof, is optimized. In this case, a brief force curve is generated by a solenoid system with at least one force pulse on the endoscopy capsule, the direction of the force generated being substantially perpendicular to the surface of the liquid.

In one advantageous embodiment, the force pulse is wherein substantially stepped, ramp-like, triangular or spline-like trend, the terms "stepped", "ramp-like", "triangular" and "spline-like" referring to the trend of the force generated. The specific shape of the profiles, in particular the stepped force pulses, has the advantage that as a result only relatively low magnetic forces have to be applied for complete immersion.

In one embodiment of the method, an odd number of force pulses is generated onto the capsule, the direction of the force of each odd force pulse facing into the liquid, so that an at least partial dipping of the endoscopy capsule into the liquid is brought about, whilst the direction of the force of each even force pulse faces out of the liquid, so that an at least partial emersion of the endoscopy capsule from the liquid is brought about.

In one alternative embodiment, an even number of force pulses is generated, the direction of the force of each odd force pulse facing out of the liquid, so that an at least partial emersion of the endoscopy capsule out of the liquid is brought about, whilst the direction of the force of each even force pulse faces into the liquid, so that an at least partial dipping of the endoscopy capsule into the liquid is brought about.

Both the embodiment with an odd number of force pulses and the alternative with an even number of force pulses proves advantageous, as the size of the amplitudes of the force pulses required for immersion is markedly less relative to the method with only one force pulse.

Advantageously, the sizes of the amplitudes of the force pulses and the trend of the force pulses over time are adapted to an oscillation resonance of a spring-mass system, the spring component of the spring-mass system being determined by the surface tension of the liquid surrounding the capsule, and the mass component including the mass of the endoscopy capsule and the mass of a component of the liquid surrounding the endoscopy capsule which is moved with the endoscopy capsule. As a result, it is achieved that the force pulses may be optimized, so that firstly a complete immersion is guaranteed and secondly only the minimum required currents have to be applied for supplying current to the coils of the solenoid system, so that an overdimensioning of the system is therefore superfluous.

The brief force curve is calculated in advance, depending on parameters characterizing the endoscopy capsule, in particular the geometry, surface characteristics and alignment of the capsule longitudinal axis relative to the water surface, and the parameters characterizing the liquid, in particular temperature, chemical composition, clarity and viscosity, such that after the brief force curve has been generated the endoscopy capsule is completely immersed and is located just below the surface of the liquid in a floating state.

Advantageously, the brief force curve is automatically generated after being triggered by an operator. Thus it is ensured that, in particular, the sizes of the forces of the force curve are correctly set and the forces acting on the capsule are discontinued in good time, so that the capsule starts to float below the surface and does not strike, for example, the opposing stomach wall.

Moreover, in one particular embodiment it is determined automatically, in particular by a capsule motion model, whether the endoscopy capsule is located right on the surface of the liquid or whether the endoscopy capsule is completely immersed. Also the operator is able to predetermine manually whether the endoscopy capsule is located right on the surface of the liquid or whether the endoscopy capsule is completely immersed. The brief force curve may not be generated when the endoscopy capsule is already completely immersed. This embodiment provides the advantage of increased safety. Moreover, the application of the brief force curve which is adapted to the mechanical resonance of the capsule on the liquid surface, is only worthwhile when the capsule is located on the liquid surface. Otherwise, this force curve may cause an uncontrolled or even erratic movement of the capsule. The capsule inadvertently striking the stomach wall, for example, and/or leaving in an uncontrolled manner the capsule position which has been selected by the long-distance images would not be excluded.

A device for implementing the method for completely immersing an endoscopy capsule floating on a surface of a liquid into the liquid by separating the endoscopy capsule from the surface of the liquid includes a solenoid system for generating a magnetic field and/or a magnetic gradient field for magnetic guidance of the endoscopy capsule and a control unit. The endoscopy capsule includes a fixedly integrated magnetic element with a magnetic dipole moment. Navigation software is located in the control unit for controlling the supply of current to the individual coils of the solenoid system and further software is implemented for controlling the supply of current to the individual coils of the solenoid system, the further software implementing the method.

Advantageously, the further software includes a capsule motion model by which, assuming a defined initial state of the endoscopy capsule and depending on magnetic forces on the endoscopy capsule generated by the solenoid system, it may be determined whether the endoscopy capsule is located right on the surface of the liquid or whether the endoscopy capsule is completely immersed.

Alternatively or additionally, the control unit has an input device by which an operator is able to predetermine manually whether the endoscopy capsule is located right on the surface of the liquid or whether the endoscopy capsule is completely immersed.

The complete immersion is wherein the water surface, below which the capsule is intended to be immersed, closes over the capsule.

BRIEF DESCRIPTION OF THE DRAWINGS

These and other aspects and advantages will become more apparent and more readily appreciated from the following description of the exemplary embodiment, taken in conjunction with the accompanying drawings of which.

DETAILED DESCRIPTION OF THE PREFERRED EMBODIMENT

Figure 1A:
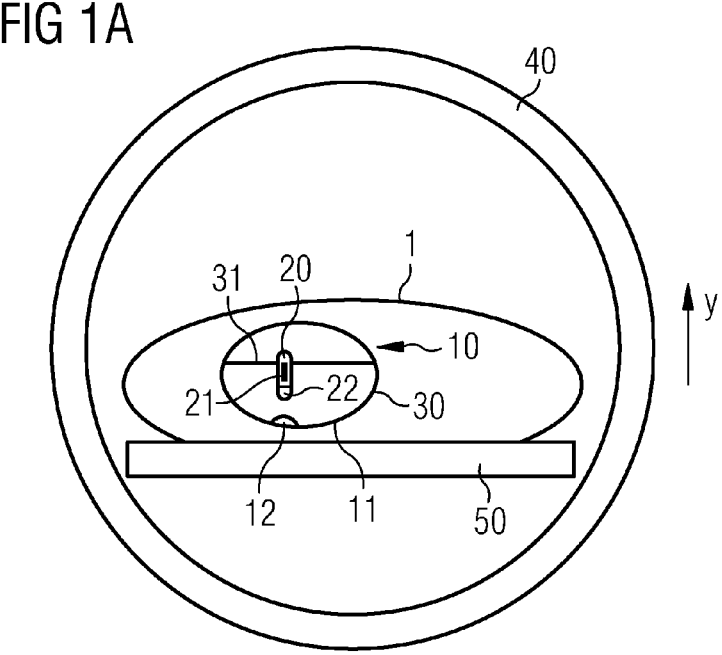
FIG. 1A is a schematic cross-section in a view which is not to scale through the stomach of a patient positioned in a solenoid arrangement.

Reference will now be made in detail to the preferred embodiments, examples of which are illustrated in the accompanying drawings, wherein like reference numerals refer to like elements throughout.

FIG. 1A shows the stomach 10 of a patient 1 in a view which is not to scale. An endoscopy capsule 20 with a permanent magnet 21 for carrying out a stomach screening is located in the stomach 10. The stomach 10 is partially filled with water 30 and the endoscopy capsule 20 floats on the water surface 31. The longitudinal axis of the endoscopy capsule 20 is oriented in FIG. 1A in the y-direction. The longitudinal axis of the endoscopy capsule 20 and the y-direction do not have to coincide, but may be at an angle of up to approximately 70° relative to one another. The y-direction is defined hereinafter as the direction which is perpendicular to the water surface 31. Thus the positive y-direction is oriented out of the water 30. Accordingly, a movement in the negative y-direction equates to the endoscopy capsule 20 being dipped in and/or immersed whilst a movement of the capsule 20 in the positive y-direction is equivalent to an emersion.

Figure 1B:
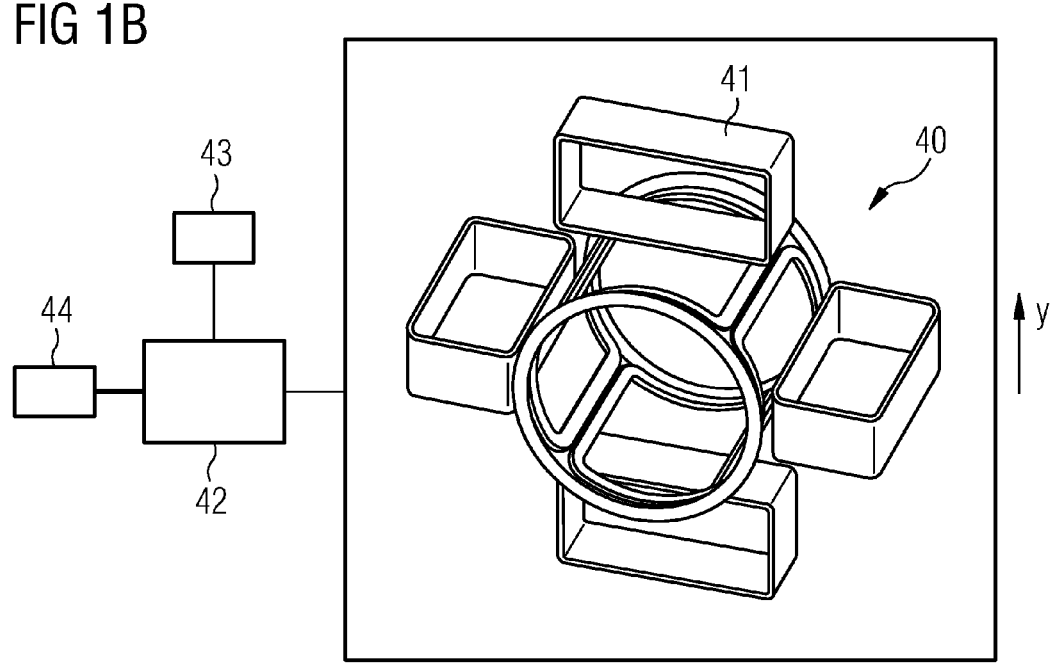
FIG. 1B is a block diagram and perspective view of a suitable solenoid arrangement for carrying out the method.

For the examination, the patient 1 lies on an examination table 50 and is positioned inside a solenoid system 40 including a plurality of individual coils 41, for the sake of clarity only one of which is provided in FIG. 1B with a reference numeral. The solenoid system 40 also includes the power amplifiers, not shown. A coil system as disclosed in, for example, DE 2008 004 871 or in DE 103 40 925 B3 may be used as a solenoid system 40. A possible embodiment of the solenoid system 40 including ten individual coils 41 which is particularly suitable for navigating the endoscopy capsule 20 in the stomach 10 of the patient 1, is shown by way of example in FIG. 1B.

The solenoid system 40 is used in order to generate, via the generation of components $B_x$, $B_y$, $B_z$ of a magnetic field $\vec{B}$ and/or gradient fields of the gradient matrix $\underline{G}$, torques and/or forces F_mag and the like onto the magnetic element 21 of the endoscopy capsule 20. As the magnetic element 21 is fixedly connected to the capsule 20, the forces generated also act directly on the endoscopy capsule 20.

The magnetic forces denoted hereinafter by F_mag are thus those forces which act on the endoscopy capsule 20, by the interaction between the magnetic element 21 of the endoscopy capsule 20 and the gradient fields of the gradient matrix $\underline{G}$ generated by the solenoid system 40.

As already mentioned, for an accurate explanation of the interaction between the solenoid system 40 and the permanent magnet 21 and/or the magnetic dipole moment thereof, reference is made to DE 10 2008 004 871.

For controlling the solenoid system 40, a control unit 42 is provided in which by corresponding navigation software the supply of current to the individual coils 41 is controlled, for generating the magnetic and gradient fields. For example, an operator of the solenoid system 40 may manually influence the magnetic and gradient fields by an operating unit 43, for example a joystick, such that depending on the direction of the deflection of the joystick 43 fields are generated in specific spatial directions, it being possible for the size of the field generated to be dependent on the amplitude of the deflection of the joystick 43.

A camera 22 is integrated into the endoscopy capsule 20, the optical axis thereof being oriented in the direction of the longitudinal axis of the capsule 20. Using the camera 22 initially long-distance images of the stomach lining 11 are taken, an abnormality 12, for example an ulcer, being discovered. In order to be able to examine the abnormality 12 in more detail, close-up images have to be taken, for which the endoscopy capsule is moved in the negative y-direction closer to the abnormality 12 and finally has to be completely immersed.

In principle, for the complete immersion and separation associated therewith of the endoscopy capsule 20 from the water surface 31 it is noteworthy that the separation process is considered as a dynamic process. Assuming that the capsule 20 with the mass M initially floats on the water surface 31, and now the solenoid system 40 exerts a magnetic force F_mag on the capsule 20 in the negative y-direction, the movement of the capsule 20 depends considerably on the time characteristic of the exerted force F_mag. If F_mag is too low, the capsule 20 and the water surface 31 surrounding it sink partially downwards, but a separation of the capsule 20 from the surface 31 and a complete immersion do not take place. Instead, the capsule 20 and the water surface 31 surrounding the capsule 20 swing back up again. With insufficient force action the capsule 20 together with the surrounding water moves as a damped oscillator and/or as a damped spring-mass system with a spring constant k_surf, and a damping k_fric+ k_fricW, k_fric being the coefficient of friction of the capsule and k_fricW being the coefficient of friction of the surrounding water, and a mass M+m, M being the mass of the capsule and m the mass of the water moved therewith. The spring component of the spring-mass system is determined by the surface tension of the liquid surrounding the capsule 20, whilst the mass component includes the mass M of the endoscopy capsule 20 and the mass m of the component of liquid surrounding the endoscopy capsule 20, which is moved with the endoscopy capsule.

Only when the downward deflection of the capsule 20 and the water surface exceeds a critical value is the energy input into the water surface sufficiently great that, after separating the edge of the water from the capsule 20, the water surface is able to close over the capsule. After this separation process, the capsule 20 moves in the water as a single body with a mass M and a hydrodynamic coefficient of friction k_fric.

Figure 2B:
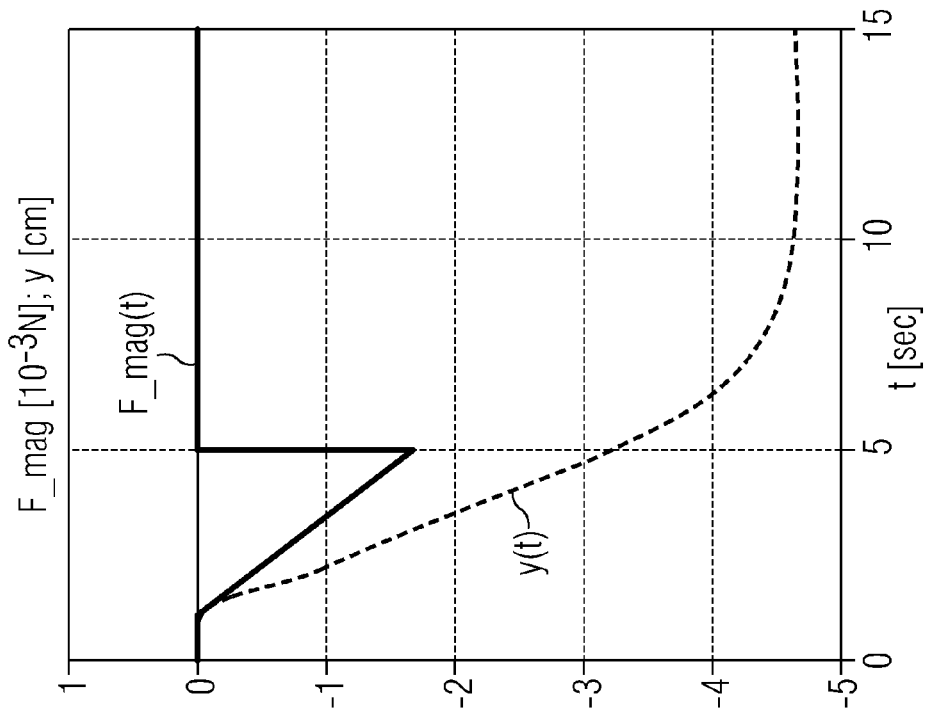
FIG. 2B is a graph of a simulation of the dependence of the capsule position on a second force curve with the same length and shape as the first force curve but with a slightly steeper ramp.
Figure 2A:
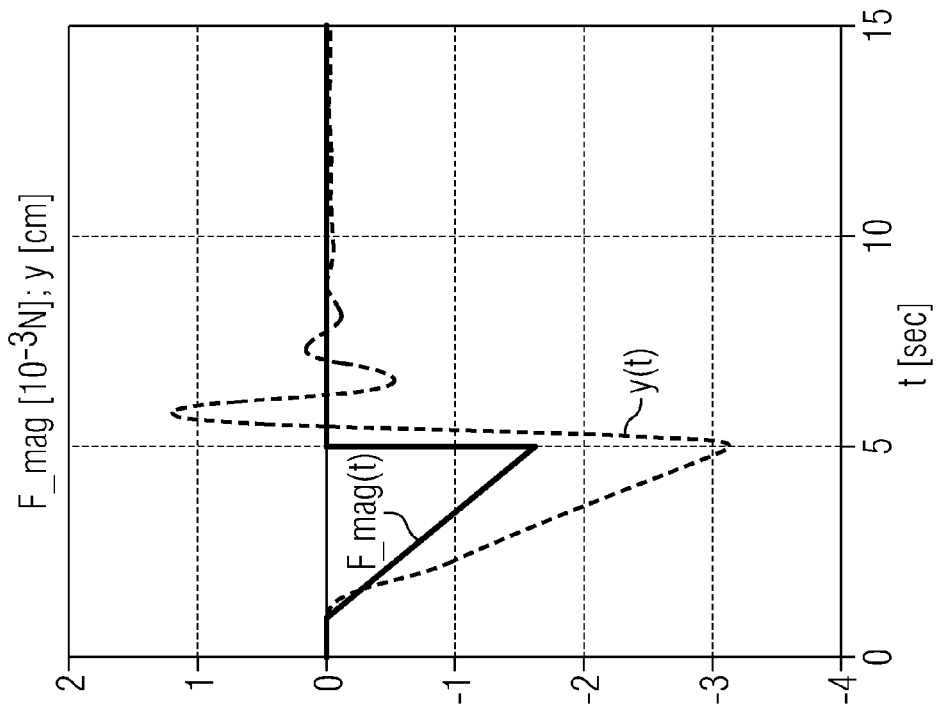
FIG. 2A is a graph of a simulation of the dependence of the capsule position on a first force curve in the form of a short ramp-shaped force pulse.

FIG. 2A shows the result of a simulation of the dependence of the capsule position y(t) in the y-direction on the force F_mag exerted on the capsule. The force curve F_mag(t) and/or the time characteristic F_mag(t) of the force F_mag is wherein the force value |F_mag(t)| gradually rises up to a maximum of 1.6 mN in a ramp-like manner and then drops to zero. The force F_mag thus acts in the negative y-direction. Also, depending on the time t, the capsule position y(t) in the y-direction is shown in FIG. 2A. The simulation shows the case in which the force F_mag is not sufficient to separate the capsule 20 from the water surface. Although the capsule 20 is immersed, after discontinuing the force F_mag it carries out an oscillating movement in the y-direction in order finally to come to rest again on the water surface 31.

FIG. 2B shows a time characteristic of the force F_mag which is substantially the same as in FIG. 2A. The ramp-like rise of the force value is, however, somewhat steeper than in FIG. 2A, so that even the maximum force value F_mag is slightly greater than in the case of FIG. 2A, i.e. greater than 1.6 mN. In this case, it results in a separation of the capsule 20 from the water surface 31 and complete immersion i.e. the water surface closes over the capsule. The capsule 20 is accordingly immersed and due to friction comes to rest at a specific depth.

Figure 2C:
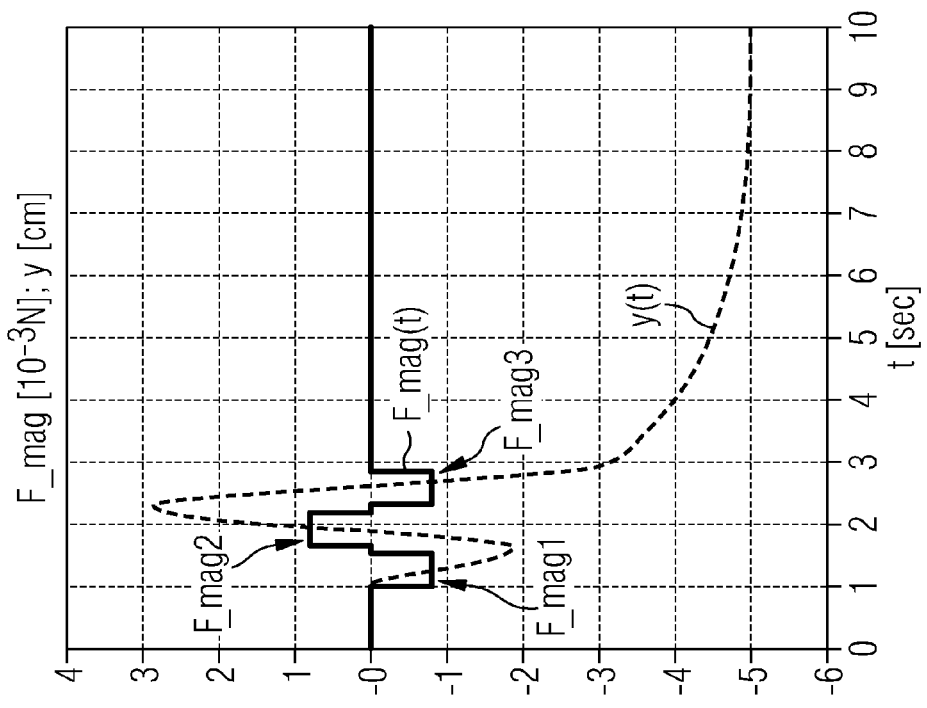
FIG. 2C is a graph of a simulation of the dependence of the capsule position on a third force curve with a stepped force pulse.

In FIG. 2C, the result of a further simulation is shown in which the time characteristic of the magnetic force F_mag generated has been altered. Instead of the ramp-like rise, in this case a force pulse F_mag(t) with a stepped profile and/or a stepped time characteristic is generated which acts in the negative y-direction.

With an ideal stepped force pulse the generated force rises at a first moment in time, abruptly from a first value which generally is at zero to a second value, the second value is then maintained for a specific time span, and at a second moment in time the force falls again abruptly back to the first value.

The trend of the force over time, however, depends directly on the trend over time of the currents flowing through the individual coils of the solenoid system 40. The trend of these coil currents, due to the inductivity of the coils and due to the technically required limited voltages of the power amplifiers (not shown) which supply current to the coils, may only be approximately stepped, whereby the trend of the generated force may also only be approximately stepped. Thus an "approximate" stepped force pulse is wherein
a) the rise in the force from the first value to the second value and/or the corresponding rise of the coil current takes place in as short a time as possible and
b) a force plateau and/or a corresponding current plateau is maintained at the level of the second value for a time period which is a multiple of the rise time.

In each case when a stepped force pulse or current pulse is mentioned hereinafter, this should be interpreted as an approximately stepped pulse. Otherwise, an ideal stepped pulse is referred to. The approximately stepped pulse is in technical terms typically produced in such a manner that, by taking into account the technical preconditions present, the minimum possible rise times are implemented from the first to the second force value. The technical preconditions in this case include the performance parameters of the power amplifiers and the characteristics of the solenoids, in particular the inductivity thereof.

Figure 2D:
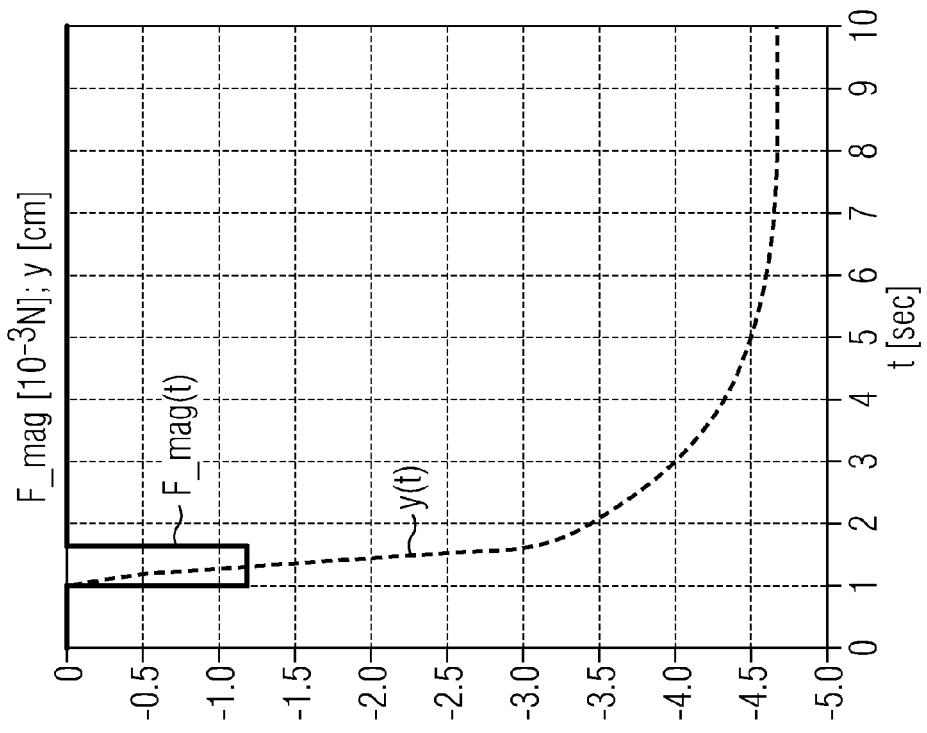
FIG. 2D is a graph of a simulation for the dependence of the capsule position on a fourth force curve with three stepped force pulses.

For the simulations, which form the basis of the diagrams of FIGS. 2C and 2D, ideal stepped force pulses have been used.

FIG. 2C shows that a complete immersion and separation from the water surface with a stepped force pulse F_mag is already possible with a force value of |F_mag|=1.2 mN. Even in this case, the capsule 20 is completely immersed and due to friction comes to rest at a specific depth.

A further reduction of the required force amplitude may be achieved by a plurality of stepped force pulses being generated in succession, in particular an odd number of force pulses being advantageous. The force pulses are adapted in their time characteristic to an oscillation resonance of the aforementioned damped spring-mass system of the capsule and the surrounding water before separation of the capsule from the water surface. In particular in this case, the sizes of the amplitudes of the force pulses and the trend over time of the force pulses are adapted to the oscillation resonance.

In this case, the direction of the force of each odd force pulse, i.e. the direction of the force of the first, third, fifth, etc. force pulse faces in the negative y-direction and/or into the liquid. The odd force pulses thus cause an immersion of the endoscopy capsule into the liquid. The direction of the force of each even force pulse, i.e. the direction of the force of the second, fourth, etc. force pulse, however, faces out of the liquid. The even force pulses accordingly cause an emersion of the endoscopy capsule from the liquid.

FIG. 2D shows in this connection the result of a simulation with a time-force curve, in which three successive force pulses F_mag1, F_mag2 and F-mag3 have been generated. The directions of the odd force pulses F-mag1 and F_mag3 face into the liquid, whilst the even force pulse F_mag2 acts in the opposing, positive y-direction. Also shown is the time characteristic y(t) of the capsule position in the y-direction. The first force pulse F_mag1 causes the endoscopy capsule to be dipped into in the liquid but not completely immersed. The second force pulse F_mag2 acts in the opposing direction and causes the emersion of the capsule from the liquid, whilst the third force pulse F_mag3 finally achieves the complete immersion of the endoscopy capsule below the surface of the liquid. As after the end of the third force pulse F_mag3 no more force acts on the capsule, the capsule does not sink in an uncontrolled manner but is decelerated by friction with the liquid and finally comes to rest just below the surface.

The plateaus of the force pulses F_mag1 to F_mag3 and/or the force values |F_mag1| to |F_mag3| which have been required in order to permit a complete immersion of the endoscopy capsule were in this case only 0.8 mN.

The simulations show that a ramp-like relatively slow force increase, as shown in FIGS. 2A and 2B, leads to a relatively high force requirement of |F_mag|>1.6 mN with the maximum F_mag(t). With an individual stepped force pulse as in FIG. 2C, a separation of the capsule from the water surface and a complete immersion has already been achieved under otherwise the same conditions, when the value of the force pulse is at least 1.2 mN. With a sequence of three successive force pulses already a value of in each case only 0.8 mN is sufficient.

In a realistic application of the method, it has to be taken into account that the generated force F_mag is sufficient for separating the capsule 20 from the water surface 31, but an additional, possibly uncontrolled downward movement of the capsule 20 is intended to be avoided. The endoscopy capsule 20 is ideally intended to float immediately after separation below the water surface 31, and in particular not strike the stomach lining 11 located below the capsule 20. Such a requirement is only able to be implemented with difficulty by manual control of the capsule 20 in which, for example by a manually operated joystick, conditions for the supply of current to the individual coils of the solenoid system 40 are produced for generating the desired magnetic fields and gradient fields, as the magnetic force F_mag for separating the capsule 20 typically has to be discontinued with a chronological accuracy of approximately 0.1 sec, in order to avoid an uncontrolled movement below the water surface 31. Moreover, the required force curve depends on the angle at which the capsule longitudinal axis is located relative to the y-direction, before and during separation from the liquid surface. Advantageously, therefore, the process of immersion of the capsule 20 i.e. the calculation and the generation of the force curve F_mag or force curves F_mag1, F_mag2, F_mag3 are automatically carried out without the operator having to intervene. This automatic process is implemented in a control unit which is connected to the solenoid system 40 and thus may generate the required force curves. Thus, in particular, as a control unit it is provided to use the control unit 42 of the solenoid system 40 which is already present, and to implement the automatic process in the control unit 42. The required action of the operator is effectively restricted to triggering the automatic process of the immersion, for example, by actuating a corresponding momentary-contact switch, or the like, of the control unit 42.

After actuating the momentary-contact switch and assuming that the endoscopy capsule 20 at this time is located on the water surface 31, using the control unit 42 a brief force curve F_mag(t) is generated which causes the capsule 20 to be completely immersed below the water surface 31 and then remain just below the water surface 31 in a floating state. A force curve corresponding to a desired force desired by the operator, which is predetermined by the operator by the operating unit 43 as disclosed above and which permits the desired navigation of the capsule 20 underwater, may be associated with this brief force curve which may include one of the force curves shown in FIGS. 2B to 2D. For example, in the case of the examination according to FIG. 1A it could be provided to move the capsule 20 further in the y-direction in order to be able to generate a close-up image of the abnormality 12.

The brief force curve is characterized relative to the normal navigation of the capsule, amongst other things, by greater magnetic forces being able to be generated, magnetic forces of a maximum of 0.2 mN to 0.3 mN typically being sufficient. As a result, with normal, manual navigation the capsule is prevented from being subjected to forces which are too high and moving too rapidly.

The control unit 42 has already been introduced for controlling the solenoid system 40. The control unit 42 may additionally be used to determine whether the endoscopy capsule 20 is right on the water surface 31 or whether the capsule 20 is completely immersed. To this end, corresponding software is implemented in the control unit 42.

In the software in the control unit 42, for example, a simple motion model of the capsule 20 is stored by which, assuming that an initial position of the capsule 20 is known, the capsule position may be calculated depending on the forces exerted on the capsule 20. Based on a defined initial state of the capsule 20, which includes an initial position and alignment of the capsule 20, and by using the control commands, for example received by the joystick 43, i.e. the direction and amplitude of the deflection of the joystick 43, the motion model determines the approximate y-position of the capsule relative to the initial position and, in particular, whether the capsule 20 floats on the water surface 31 or not. In this case, from an initial moment in time, the entire time characteristic of the magnetic forces acting on the capsule are taken into account. Typically, at the start of the screening procedure the capsule is on the water surface and/or moved there magnetically. It is advantageous for implementing such a motion model that if over a certain time period no inputs are made by the operator via the joystick 43 or via a different operating unit, such as for example a keyboard, the operating mode of the control unit 42 is automatically switched to one in which the endoscopy capsule 20 is pulled towards the water surface 31. Then it may reliably be assumed that the capsule 20 is located on the surface 31, so that a defined state of: "endoscopy capsule is floating on the water surface" is achieved.

Alternatively or additionally, the state and/or initial state of the capsule 20 is indicated to the operator via a graphic user interface (GUI), i.e. specifically whether the capsule 20 is floating on the water surface 31 or whether it is completely immersed. Using a corresponding input unit 44, for example by a key or a foot-operated switch, the operator may alter manually the state of the capsule 20 received in the software and displayed on the GUI, as required. If it is displayed on the GUI, for example, that the capsule 20 is completely immersed, but the operator is certain that the capsule 20 is floating, by an actuation of the input unit 44 the operator may correct the accepted state of the capsule 20 in the software and thus establish a suitable initial state for the motion model.

The above-described force pulses have either a ramp-like or a stepped profile and/or trend over time. Naturally also conceivable are force pulses with, for example, a symmetrical or asymmetrical triangular profile or a sinusoidal or cosine-shaped profile. Also, the shape of the force pulses may be spline-like, i.e. as linear splines or splines of greater size. Other profile shapes are also possible, but a stepped profile has the advantage that the required maximum force and/or the required maximum current is lower than in non-stepped profiles.

For calculating the individual force pulses with the purpose that the capsule is completely immersed and comes to rest just below the surface, the force curve is initially defined as a sequence of 3 approximately stepped force pulses, for example, all three pulses having the same chronological length and amplitude. Accordingly, two freely selectable parameters, namely the length and amplitude of the individual pulse, remain to be determined. This determination is best carried out experimentally and namely depending on the geometry and surface material specifically for the particular capsule which is intended to be actually used in a specific examination. When determining the parameters, a dependence on the capsule alignment in the water and/or on the water surface may also possibly play a role. The influence of the water, for example depending on the temperature and possible contamination, is probably low as long as no additives such as for example foaming agents are used.

The force curves determined experimentally are stored in the software of the control unit 42, for example in the form of "look-up tables" which contain parameters which explicitly characterize the force curve.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV*, 358 F3d 870, 69 USPQ2d 1865 (Fed. Cir. 2004).

The invention claimed is:

1. A method for completely immersing an endoscopy capsule, floating on a surface of a liquid, by separating the endoscopy capsule from the surface of the liquid, the endoscopy capsule having a fixedly integrated magnetic element with a magnetic dipole moment, said method comprising:

generating, in a solenoid system, at least one of a magnetic field and a magnetic gradient field for magnetic guidance of the endoscopy capsule, having a brief force curve with at least one force pulse onto the fixedly integrated magnetic element of the endoscopy capsule where amplitude sizes of the force pulses and a trend over time of the force pulses are adapted to an oscillation resonance of a spring-mass system, the force pulses having a direction substantially perpendicular to the surface of the liquid.

2. The method as claimed in claim 1, wherein the force pulse has a substantially stepped, ramp-like, triangular or spline-like trend over time.

3. The method as claimed in claim 2, wherein the brief force curve has an odd number N of force pulses where N>1, the direction of the force of each odd force pulse facing into the liquid, and an at least partial dipping of the endoscopy capsule into the liquid being brought about, and the direction of the force of each even force pulse facing out of the liquid, and an at least partial emersion of the endoscopy capsule from the liquid being brought about.

4. The method as claimed in claim 3, wherein the spring-mass system has a spring component determined by a surface tension of the liquid surrounding the endoscopy capsule, and a mass component formed by an endoscopy capsule mass and a liquid mass of a component of the liquid surrounding the endoscopy capsule which is moved with the endoscopy capsule.

5. The method as claimed in claim 2, wherein the brief force curve has an even number N of force pulses where N>1, the direction of the force of each odd force pulse facing out of the liquid, and an at least partial emersion of the endoscopy capsule from the liquid being brought about, and the direction of the force of each even force pulse facing into the liquid, and an at least partial dipping of the endoscopy capsule into the liquid being brought about.

6. The method as claimed in claim 5, wherein the spring-mass system has a spring component determined by a surface tension of the liquid surrounding the endoscopy capsule, and a mass component formed by an endoscopy capsule mass and a liquid mass of a component of the liquid surrounding the endoscopy capsule which is moved with the endoscopy capsule.

7. The method as claimed in claim 2, wherein the brief force curve is calculated in advance, depending on parameters characterizing the endoscopy capsule, including geometry, surface characteristics and alignment of a longitudinal axis of the capsule relative to the surface of the liquid, and depending on parameters characterizing the liquid, including temperature, chemical composition, clarity and viscosity, such that after the brief force curve has been generated the endoscopy capsule is completely immersed and is located just below the surface of the liquid.

8. The method as claimed in claim 7, wherein the brief force curve is automatically generated after being triggered by an operator.

9. The method as claimed in claim 8, further comprising automatically determining, based on a capsule motion model, whether the endoscopy capsule is located right on the surface of the liquid or whether the endoscopy capsule is completely immersed.

10. The method as claimed in claim 8, wherein the operator is able to predetermine manually whether the endoscopy capsule is located right on the surface of the liquid or whether the endoscopy capsule is completely immersed.

11. The method as claimed in claim 7, wherein the brief force curve cannot be generated when the endoscopy capsule is already completely immersed.

12. A device for completely immersing an endoscopy capsule floating on a surface of a liquid by separating the endoscopy capsule from the surface of the liquid, the endoscopy capsule having a fixedly integrated magnetic element with a magnetic dipole moment, said device comprising:

a solenoid system having coils generating at least one of a magnetic field and a magnetic gradient field for magnetic guidance of the endoscopy capsule; and a control unit with hardware and software individually controlling current supply to the coils of the solenoid system, to generate at least one of the magnetic field and the magnetic gradient field for magnetic guidance of the endoscopy capsule, having a brief force curve with at least one force pulse onto the fixedly integrated magnetic element of the endoscopy capsule where amplitude sizes of the force pulses and a trend over time of the force pulses are adapted to an oscillation resonance of a spring-mass system, the force pulses having a direction substantially perpendicular to the surface of the liquid.

13. The device as claimed in claim 12, wherein the software includes a capsule-motion model which assumes a defined initial state of the endoscopy capsule and depending on magnetic forces on the endoscopy capsule generated by said solenoid system determines whether the endoscopy capsule is located right on the surface of the liquid or whether the endoscopy capsule is completely immersed.

14. The device as claimed in claim 13, further comprising an input unit, connected to the control unit, by which an operator is able to predetermine manually whether the endoscopy capsule is located right on the surface of the liquid or whether the endoscopy capsule is completely immersed.

15. A method for completely immersing an endoscopy capsule floating on a surface of a liquid, said method comprising:

separating the endoscopy capsule from the surface of the liquid and completely immersing the endoscopy capsule to a depth below the surface of the liquid in a suspended state, the endoscopy capsule having a fixedly integrated magnetic element with a magnetic dipole moment;

generating, in a solenoid system, at least one of a magnetic field and a magnetic gradient field for magnetic guidance of the endoscopy capsule, having a brief force curve with at least one force pulse applied to the fixedly integrated magnetic element of the endoscopy capsule; and modeling amplitude sizes of the force pulses and a trend over time of the force pulses to an oscillation resonance of a spring-mass system, the force pulses having a direction substantially perpendicular to the surface of the liquid.

16. A device for completely immersing an endoscopy capsule floating on a surface of a liquid, said device comprising:

a solenoid system having coils generating at least one of a magnetic field and a magnetic gradient field for magnetic guidance of the endoscopy capsule; and a control unit with hardware and software individually controlling current supply to the coils of the solenoid system to:

separate the endoscopy capsule from the surface of the liquid and completely immerse the endoscopy capsule to a depth below the surface of the liquid in a suspended state, the endoscopy capsule having a fixedly integrated magnetic element with a magnetic dipole moment;

generate at least one of the magnetic field and the magnetic gradient field for magnetic guidance of the endoscopy capsule, having a brief force curve with at least one force pulse applied to the fixedly integrated magnetic element of the endoscopy capsule, and model amplitude sizes of the force pulses and a trend over time of the force pulses to an oscillation resonance of a spring-mass system, the force pulses having a direction substantially perpendicular to the surface of the liquid.

* * * * *